United States Patent
Nekludoff et al.

(10) Patent No.: US 6,395,264 B1
(45) Date of Patent: *May 28, 2002

(54) LOW VOC HAIR SPRAY COMPOSITIONS HAVING ENHANCED STYLING BENEFITS

(75) Inventors: Natalia Nekludoff; Diane Dabkowski, both of Chicago; Tirucherai Vasudevan, Lake Zurich, all of IL (US)

(73) Assignee: Unilever Home & Personal Care USA division of Conopco, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/307,060

(22) Filed: May 7, 1999

(51) Int. Cl.$^7$ .................................. A61K 7/11
(52) U.S. Cl. ............... 424/70.11; 424/70.1; 424/70.12; 424/70.16; 424/70.22; 424/47; 424/DIG. 2; 514/63; 514/945
(58) Field of Search ....................... 424/47, 70.1, 70.11, 424/70.12, 70.16, 70.22, DIG. 2; 514/63, 945

(56) References Cited

U.S. PATENT DOCUMENTS

| | | | |
|---|---|---|---|
| 4,445,521 A | | 5/1984 | Grollier et al. |
| 4,897,262 A | * | 1/1990 | Nandagini et al. |
| 5,164,177 A | | 11/1992 | Bhatt et al. |
| 5,374,420 A | | 12/1994 | Gerstein |
| 6,007,793 A | * | 12/1999 | Bhatt et al. |
| 6,017,860 A | * | 1/2000 | Sajic et al. |
| 6,056,946 A | * | 5/2000 | Crudele et al. |
| 6,106,808 A | * | 8/2000 | Bhatt et al. |
| 6,106,809 A | * | 8/2000 | Bhatt et al. |
| 6,113,881 A | * | 9/2000 | Bhatt et al. |
| 6,132,704 A | * | 10/2000 | Bhatt et al. |
| 6,274,129 B1 | * | 8/2001 | Bhatt et al. |
| 6,284,225 B1 | * | 9/2001 | Bhatt et al. |

FOREIGN PATENT DOCUMENTS

| | | | |
|---|---|---|---|
| EP | 838 211 | * | 4/1998 |
| EP | 838 212 | * | 4/1998 |

* cited by examiner

*Primary Examiner*—Raj Bawa
(74) *Attorney, Agent, or Firm*—Matthew Boxer

(57) ABSTRACT

An aqueous non-aerosol hair styling composition having 55% or less VOC content, said composition comprising (i) a water soluble or dispersable fixative polymer of about 10 to about 1000 Kilo Daltons and in an amount ranging from 1% to 40% by weight of the composition; (ii) a neutralizing agent in an amount ranging from 0.1 to 10% by weight and selected from the group consisting of 2-amino, 2-methyl, 1-propanol, dimethyl stearamine, sodium hydroxide, and potassium hydroxide; (iii) a surfactant in an amount ranging from 0.01% to 5% by weight and selected from the group consisting of sodium dioctyl sulfo succinate, sodium dodecyl sulfate, cocoamidopropyl betaine, and sodium laureth sulfate; (iv) a salt ranging from 0.01% to 10% by weight and selected from the group consisting of sodium benzoate, and magnesium acetate; (v) an alcohol ranging from 10% to 90% by weight; and (vi) water ranging from 10% to 90% by weight.

7 Claims, No Drawings

LOW VOC HAIR SPRAY COMPOSITIONS HAVING ENHANCED STYLING BENEFITS

BACKGROUND OF THE INVENTION

Regulations and laws designed to protect the environment, are leading to the production of hair care spray products which have lower volatile organic compounds (VOC) content than the current commercial products.

This invention relates to 55% VOC (and lower VOC) hair spray compositions that provide hold and feel properties similar to or better than that of the current 80% VOC hair sprays. The performance characteristics of hair sprays suffer as the VOC level is reduced from 80% to 55% in the product. Therefore, maintaining or improving the performance characteristics of 80% VOC product in 55% VOC (and lower VOC) products affords hairspray products which have good characteristics and are more environmentally friendly.

SUMMARY OF THE INVENTION

As noted above, the performance characteristics of hair sprays generally suffer as the VOC level is reduced from 80% to 55% in the product. The purpose of this invention is to at least maintain, if not improve, the performance characteristics of the 80% VOC system in the 55% VOC product.

In the present invention, the deterioration of the spray characteristics of a hydroalcoholic solution containing the hair spray resin which occurred as the alcohol content was reduced from 80 to 55% was offset by incorporation of a unique combination of hydrocarbon based surfactants and an organic salt. The same benefit can be obtained in aqueous systems.

In the present invention, the hydrocarbon surfactant is selected from the group consisting of: sodium dioctyl sulfo succinate, sodium dodecyl sulfate, cocoamidopropyl betaine, and sodium laureth sulfate, and the like.

In the present invention, the organic salt is selected from the group consisting of: sodium benzoate, magnesium acetate, and the like.

The invention relates to an aqueous or hydroalcoholic, non-aerosol or aerosol hair spray composition containing a water soluble or dispersable fixative polymer in an amount from about 1% to about 40% by weight of the composition, a neutralizing agent in an amount from about 0.1 to about 10 wt %, a hydrocarbon based surfactant in an amount from about 0.01% to about 5% by weight, a salt from about 0.01% to about 10% by weight, alcohol from about 10% to about 90% by weight, a propellant from about 0 to about 80% by weight, and water from about 10% to about 90% by weight of the composition.

U.S. patents in this area of technology are:
U.S. Pat. Nos. 5,374,420 and 5,164,177.

DETAILED DESCRIPTION OF THE INVENTION

As used herein, % means weight % of the total composition unless otherwise indicated.

The starting materials set forth herein are either known or can be prepared according to known methods. The compositions of the invention can be prepared either by known methods or by methods analogous to known methods.

As noted above, in the present invention, the deterioration of the spray characteristics of a hydroalcoholic solution containing the hair spray resin which occurred as the alcohol content was reduced from 80 to 55% was offset by incorporation of a unique combination of hydrocarbon based surfactants and an organic salt. The same benefit can be obtained in aqueous systems.

In the present invention, the hydrocarbon surfactant is selected from the group consisting of: sodium dioctyl sulfo succinate, sodium dodecyl sulfate, cocoamidopropyl betaine, and sodium laureth sulfate, and the like. In fact any hydrocarbon based surfactant suitable for use in hairspray compositions may be employed in the compositions of the invention. Other examples of anionic surfactants are sodium dinonyl sulfo succinate, sodium decyl sulfate, sodium alpha olefin sulfonate and the like. Nonionic and cationic surfactants may also be employed.

In the present invention, the organic salt is selected from the group consisting of: sodium benzoate, magnesium acetate, sodium acetate, sodium citrate, potassium acetate, sodium salicylate, sodium tartrate, sodium phenylsalicylate, sodium oxalate, sodium adipate, sodium butyrate, sodium caprate, sodium caproate, sodium maleate, sodium malate, sodium malonate, sodium phthalate, sodium propionate, sodium pyruvate, sodium fumarate, and the like.

In the present invention, the neutralizing agent is selected from the group consisting of: 2-amino, 2-methyl, 1-propanol, 2-amino, 2-methyl, 1,3-propanediol, dimethyl stearamine, histidine, tris(hydroxymethyl)aminomethane, triethanol amine, sodium hydroxide, potassium hydroxide and the like.

In the present invention, the soluble or dispersible fixative polymer is selected from the group consisting of: vinyl and acrylic based resins and polyurethane resins. Specific resins include, but are not limited to, acrylamide copolymers, acrylate copolymers, which may or may not be modified by introduction of a quaternary ammonium group. Other fixative resins are described in copending U.S. patent application Ser. No. 08/717,113 to Bhatt et al , filed Sep. 20, 1996, which is hereby incorporated by reference. The use of resins or polymers in hairsprays is known as summarized in Grollier et al U.S. Pat. No. 4,445,521 which is hereby incorporated by reference. The molecular weight of the polymer has a preferred range of about 10,000 to about 1 million Daltons, a more preferred range is about 20,000 to about 500,000 Daltons and the most preferred range is about 30,000 to about 300,000.

In the present invention, the inorganic salt is selected from the group consisting of chloride, sulfate, and nitrate salts of sodium, magnesium and ammonium and the like.

In the present invention, the alcohol, if present, is selected from the group consisting of: ethanol, isopropanol, and the like.

In the present invention, the propellant, if present, is selected from the group consisting of: trichlorofluoromethane, dichlorodiflouromethane, dichlorotetraflouromethane, methyl acetate, dimethyl ether, propane, n-butane, isobutane and mixtures thereof, and like propellants.

The compositions of the present invention also include silicone conditioning agents such as cyclomethicone, dimethicone copolyol and the like.

Other optional ingredients which can be included in hairspray compositions of the invention are preservatives such as benzyl alcohol, methyl paraben, propyl paraben, or imidazolidinylurea, cationic conditioners such as cetyl ammonium chloride, stearyl dimethyl benzyl ammonium chloride, coloring agents, chelating agents, such aminetetraacetic acid, plasticizers such as glycols, phthalate esters and glycerines, silicones, emollients, lubricants and penetrants such as various lanolin compounds, protein hydrosylates, and other protein derivatives ethylene adducts and polyoxyethylene cholesterol.

Non-Aerosol Compositions

The invention relates to an aqueous or hydroalcoholic, non-aerosol or aerosol hair spray composition containing a water soluble or dispersable fixative polymer in an amount from about 1% to about 40% by weight of the composition, a neutralizing agent in an amount from about 0.1 to about 10 wt %, a hydrocarbon based surfactant in an amount from about 0.01% to about 5% by weight, a salt from about 0.01% to about 10% by weight, alcohol from about 10% to about 90% by weight and water from about 10% to about 90% by weight of the composition.

Preferred ranges of a water soluble or dispersible fixative polymer are about 1 to about 40% by weight of the composition, more preferably about 2 to about 20%, and most preferably about 3 to about 10%.

Preferred ranges of a neutralizing agent are about 0.1 to about 10% by weight of the composition, more preferably about 0.25% to about 5%, and most preferably about 0.5% to about 2.5%.

Preferred ranges of a hydrocarbon based surfactant are about 0.01% to about 5% by weight of the composition, more preferably about 0.05% to about 2.5%, and most preferably about 0.1% to about 1.0%.

Preferred ranges of the salt about 0.01 to about 10% by weight of the composition, more preferably about 0.05% to about 5%, and most preferably about 0.1% to about 1%.

Preferred ranges of silicone conditioning agents are 0.001 to about 10% by weight of the composition, preferably from 0.01 to about 5%.

Also preferred are compositions of the invention in which the polymer is a ethyl acrylate, methyl methacrylate and methacrylic acid copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a terpolymer of ethyl acrylate, t-butyl acrylate and methacrylic acid in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is a octyl acrylamide, acrylates and butylaminoethyl methacrylate copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a methacrylic acid, n-butyl acrylate and methyl methacrylate copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is a methacrylic acid, n-butyl acrylate and ethyl methacrylate copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is a butyl acrylate, methyl methacrylate, hydroxyethyl methacrylate and methacrylic acid copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a vinyl acetate, crotonates and vinyl neodecanoate copolymer in the molecular weight range of about 10 to about 1000 Kilo Daltons, preferably about 20 to 500 Kilo Daltons, and most preferably about 50 to about 300 Kilo Daltons, Also preferred are compositions of the invention in which the polymer is a butyl ester of vinyl methyl ether and maleic anhydride copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is an ethyl ester of vinyl methyl ether and maleic anhydride copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer consists of polystyrene sulfonate monomers in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer consists of 1-vinyl-2-pyrrolidone monomers in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a vinyl acetate and vinylpyrrolidone copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a vinylcaprolactam homopolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a quaternary ammonium polymer formed by the reaction of diethyl sulfate and a copolymer of vinyl pyrrolidone and dimethyl aminoethylmethacrylate in the molecular weight range of about 10 to about 1000 Kilo Daltons, preferably about 20 to 500 Kilo Daltons, and most preferably about 50 to about 300 Kilo Daltons.

Also preferred are compositions of the invention in which the hydrocarbon surfactant is an anionic surfactant.

Also preferred are compositions of the invention in which the anionic surfactant is sodium dioctyl sulfosuccinate or its acid form.

Also preferred are compositions of the invention in which the anionic surfactant is magnesium dioctyl sulfosuccinate or its acid form.

Also preferred are compositions of the invention in which the anionic surfactant is ammonium dioctyl sulfosuccinate or its acid form.

Also preferred are compositions of the invention in which the anionic surfactant is sodium dodecyl sulfate or its acid form.

Also preferred are compositions of the invention in which the anionic surfactant is magnesium dodecyl sulfate or its acid form.

Also preferred are compositions of the invention in which the anionic surfactant is ammonium dodecyl sulfate or its acid form.

Also preferred are compositions of the invention in which the anionic surfactant is sodium laureth sulfate or its acid form.

Also preferred are compositions of the invention in which the anionic surfactant is magnesium laureth sulfate or its acid form.

Also preferred are compositions of the invention in which the anionic surfactant is ammonium laureth sulfate or its acid form.

Also preferred are compositions of the invention in which the hydrocarbon based surfactant is a zwitterionic surfactant.

Also preferred are compositions of the invention in which the zwitterionic surfactant is cocoamidopropyl betaine.

Also preferred are compositions of the invention in which the salt is an organic salt.

Also preferred are compositions of the invention in which the organic salt is sodium benzoate.

Also preferred are compositions of the invention in which the organic salt is magnesium benzoate.

Also preferred are compositions of the invention in which the organic salt is sodium acetate.

Also preferred are compositions of the invention in which the organic salt is magnesium acetate.

Also preferred are compositions of the invention in which the salt is an inorganic salt.

Also preferred are compositions of the invention in which the inorganic salt is sodium chloride.

Also preferred are compositions of the invention in which the inorganic salt is magnesium chloride.

Also preferred are compositions of the invention in which the alcohol is ethanol.

Also preferred are compositions of the invention in which the alcohol is isopropanol.

Also preferred are compositions of the invention further including silicone based surfactants in an amount from 0.01% to 5% by weight of the composition.

Also preferred are compositions of the invention in which the silicone based surfactant is dimethicone copolyol.

Also preferred are compositions of the invention in which the silicone based surfactant is cyclomethicone.

Also preferred are compositions of the invention in which the neutralizing agent is 2-amino, 2-methyl, 1-propanol.

Also preferred are compositions of the invention in which the neutralizing agent is dimethyl stearamine.

Also preferred are compositions of the invention in which the neutralizing agent is sodium hydroxide.

Also preferred are compositions of the invention in which the neutralizing agent is potassium hydroxide.

Aerosol Compositions

Also preferred are compositions of the invention which are aqueous aerosol hair styling aid or mousse compositions containing a water soluble or dispersable fixative polymer in an amount from 1% to 40% by weight of the composition, a neutralizing agent in an amount from 1 to 10 wt %, a hydrocarbon based surfactant in an amount from 0.01% to 5% by weight, a salt from 0.01% to 10% by weight, alcohol from 10% to 90% by weight and water from 10% to 90% by weight of the composition and a liquified propellant gas from 5% to 60% by weight.

Also preferred are compositions of the invention in which the polymer is an ethyl acrylate, methyl methacrylate and methacrylic acid copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a terpolymer of ethyl acrylate, t-butyl acrylate and methacrylic acid in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is a octyl acrylamide, acrylates and butylaminoethyl methacrylate copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a methacrylic acid, n-butyl acrylate and methyl methacrylate copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is a methacrylic acid, n-butyl acrylate and ethyl methacrylate copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is a butyl acrylate, methyl methacrylate, hydroxyethyl methacrylate and methacrylic acid copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a vinyl acetate, crotonates and vinyl neodecanoate copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a butyl ester of vinyl methyl ether and maleic anhydride copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer is an ethyl ester of vinyl methyl ether and maleic anhydride copolymer in the molecular weight range about 10 to about 1000 Kilo Daltons, preferably about 20 to 500 Kilo Daltons, and most preferably about 50 to about 300 Kilo Daltons.

Also preferred are compositions of the invention in which the polymer consists of polystyrene sulfonate monomers in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer consists of 1-vinyl-2-pyrrolidone monomers in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a vinyl acetate and vinylpyrrolidone copolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a vinylcaprolactam homopolymer in the molecular weight range of about 10 to about 1000 Kilo Daltons, preferably about 20 to 500 Kilo Daltons, and most preferably about 50 to about 300 Kilo Daltons.

Also preferred are compositions of the invention in which the polymer is a quaternary ammonium polymer formed by the reaction of diethyl sulfate and a copolymer of vinyl pyrrolidone and dimethyl aminoethylmethacrylate in the molecular weight range of about 10 to about 1000 Kilo Daltons, preferably about 20 to 500 Kilo Daltons, and most preferably about 50 to about 300 Kilo Daltons.

Also preferred are compositions of the invention in which the hydrocarbon surfactant is an anionic surfactant.

Also preferred are compositions of the invention in which the anionic surfactant is sodium dioctyl sulfosuccinate or its acid form.

Also preferred are compositions of the invention in which the anionic surfactant is magnesium dioctyl sulfosuccinate or its acid form.

Also preferred are compositions of the invention in which the anionic surfactant is ammonium dioctyl sulfosuccinate or its acid form.

Also preferred are compositions of the invention in which the anionic surfactant is sodium dodecyl sulfate or its acid form.

Also preferred are compositions of the invention in which the anionic surfactant is magnesium dodecyl sulfate or its acid form.

Also preferred are compositions of the invention in which the anionic surfactant is ammonium dodecyl sulfate or its acid form.

Also preferred are compositions of the invention in which the anionic surfactant is sodium laureth sulfate or its acid form.

Also preferred are compositions of the invention in which the anionic surfactant is magnesium laureth sulfate or its acid form.

Also preferred are compositions of the invention in which the anionic surfactant is ammonium laureth sulfate or its acid form.

Also preferred are compositions of the invention in which the hydrocarbon based surfactant is a zwitterionic surfactant.

Also preferred are compositions of the invention in which the zwitterionic surfactant is cocoamidopropyl betaine.

Also preferred are compositions of the invention in which the salt is an organic salt.

Also preferred are compositions of the invention in which the organic salt is sodium benzoate.

Also preferred are compositions of the invention in which the organic salt is magnesium benzoate.

Also preferred are compositions of the invention in which the organic salt is sodium acetate.

Also preferred are compositions of the invention in which the organic salt is magnesium acetate.

Also preferred are compositions of the invention in which the salt is an inorganic salt.

Also preferred are compositions of the invention in which the inorganic salt is sodium chloride.

Also preferred are compositions of the invention in which the inorganic salt is magnesium chloride.

Also preferred are compositions of the invention in which the alcohol is ethanol.

Also preferred are compositions of the invention in which the alcohol is isopropanol.

Also preferred are compositions of the invention further including silicone based surfactants in an amount from 0.01% to 5% by weight of the composition.

Also preferred are compositions of the invention. The compositions in which the silicone based surfactant is dimethicone copolyol.

Also preferred are compositions of the invention in which the silicone based surfactant is cyclomethicone.

Also preferred are compositions of the invention in which the neutralizing agent is 2-amino, 2-methyl, 1-propanol.

Also preferred are compositions of the invention in which the neutralizing agent is dimethyl stearamine.

Also preferred are compositions of the invention in which the neutralizing agent is sodium hydroxide.

Also preferred are compositions of the invention in which the neutralizing agent is potassium hydroxide.

Also preferred are compositions of the invention in which the liquified propellant gas is dimethyl ether.

Also preferred are compositions of the invention in which the liquified propellant gas is a mixture of propane and butane.

Also preferred are compositions of the invention in which the liquified propellant gas is methyl acetate.

Hair spray compositions of the invention can be in the form of hair sprays, spritzes, mousses etc.

The invention also relates to a method of treating or styling hair which comprises contacting said hair with the hair spray compositions of the invention. After hair spray compositions are applied to the hair, said hair can be styled, etc. in various ways which are known in the art.

What follows are nonlimiting examples of hair spray compositions of the invention.

The materials, definitions, and performance criteria, for low VOC compositions of the invention having enhanced styling benefits are set forth just below.

Materials
Polymers
Amphomer 28-4910: Octylacrylamide, acrylates and butyl aminoethyl methacrylate copolymer with a molecular weight range of 165 to 225 Kilo Daltons from National Starch and Chemicals Co. of NJ, USA.
Amphomer LV-71: Octylacrylamide, acrylates and butyl aminoethyl methacrylate copolymer with a molecular weight range of 120 to 165 Kilo Daltons from National Starch and Chemicals Co. of NJ, USA.
HC 7801: Methacrylic acid, n-butyl acrylate and ethyl methacrylate copolymer with a molecular weight range of 50 to 100 kilo Daltons.
Resyn 28-2930: Vinyl acetate, crotonates, vinyl neodecanoate copolymer with a molecular weight range of 70 to 110 kilo Daltons from National Starch and Chemicals Co. of NJ, USA..
Neutralizer
2-amino, 2-methyl, 1-propanol from Angus Chemical Company, LA, USA.
Silicone Surfactants
Dimethicone copolyol: Silwet L-720 from Witco Corp., WV, USA
Cyclomethicone: DC 245 from Dow Corning, MI, USA
Hydrocarbon surfactants
Sodium dioctyl sulfo succinate: Monawet MO 75-E from Uniqema, NJ, USA
Sodium dodecyl sulfate: Obtained from BDH Laboratory supplies, Poole, England
Cocoamidopropyl betaine: Tegobetaine from GoldSchmidt Industries
Sodium laureth sulfate (2 moles EO): Empicol ESB 3/AQ from Albright & Wilson, IL, USA
Organic Salts
Sodium benzoate: Boric chemical, IL USA
Magnesium acetate: Aldrich, WI., USA
Propellant
Dimethyl ether: Dymel DME from DuPont Chemical Co., Wilmington, Del. USA
Definitions
Dynamic Surface Tension
A test liquid in a typical surface tension experiment is static and any surface active material would be in equilibrium. In reality, spraying and subsequent wet out on hair are both dynamic processes and are affected by the surface tension of the formulation. Any materials that are surface active need time to migrate to and organize themselves at the air-liquid interface in order to effectively lower the surface tension. Any difference in perceived static versus dynamic surface tension could result in less than optimum performance. As described below, the faster the surface tension of a composition equilibrates, the better are its hairspray characteristics.

The dynamic surface tension experiment is typically conducted using a maximum bubble pressure method. This method is based on recording the pressure required to form bubbles at a given rate/frequency in a test liquid. The surface tension is then calculated based on the measured pressure. The results are typically expressed in terms of dynamic surface tension against the surface age. Surface age is the time elapsed between the bubble formation and detachment of the bubble.

A surface age of about 10 msec is the time frame of interest for drop formation in spray process. The liquids used in hair spray applications generally reach equilibrium within 1000 msec (surface age of 1 sec.). To obtain good spray properties, the difference between the surface tension obtained at very short time scales (ex: 10 msec) and the equilibrium surface tension (obtained for example at 1000 sec or higher) should be as small as possible.

We have chosen the difference in surface tension obtained at a surface age of about 10 msec and that obtained at a surface age of about 1500 msec ($\Delta_{10-1500}$) as the criterion for comparing the performance of different hair spray solutions.

Preparation of 55% Voc Non-Aerosol Hairspray Solutions

Equipment

Fawcett Co, Model 103-A Mixer
Mettler Toledo PG5002-S balance
medium sized stir bar (optional)
beaker
transfer pipets
USA Standard Testing Sieve #100, WS Tyler Unc. 150 micrometer Procedure 1. Add item#1, SD Alcohol 40-B into a suitably sized container.
2. Begin moderate agitation using an overhead mixer or a stir bar.
3. Add item#2, neutralizer. Increase agitation to high setting until a vortex is created.
4. Add item#3, polymer, slowly directly into the vortex. Reduce mixing speed to moderate setting. Continue mixing until solution is clear.
5. Add item#4, surfactant, followed item#5, Silicone surfactant, and item#6, fragrance.
6. Add item#7, water followed by item#8, salt.
7. Continue mixing until solution is clear.
8. Conduct an alcohol correction for any alcohol which might have evaporated during the mixing process.
9. Filter solution through a 150 micron mesh filter.

The following compositions of the invention were made.

TABLE 1

55% VOC Non-Aerosol Hair Spray Compositions

| | Test Solution # | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Component | CONTROL | | | | | wt % | | | | | | |
| Ethanol | 53.0 | 55.0 | 55.0 | 55.0 | 55.0 | 55.0 | 55.0 | 55.0 | 55.0 | 55.0 | 55.0 | 55.0 |
| Isopropanol | 2.0 | — | — | — | — | — | — | — | — | — | — | — |
| 2-amino,2-methyl,1-propanol | 0.91 | 0.82 | 0.82 | 0.82 | 0.82 | 0.82 | 0.82 | 0.82 | 0.82 | 0.82 | 0.82 | 0.41 |
| Amphomer 28-4910 | 6.0 | 6.0 | 6.0 | 6.0 | 6.0 | 6.0 | 6.0 | 6.0 | 6.0 | 6.0 | 6.0 | 3.0 |
| Dimethicone copolyol | — | 0.3 | 0.3 | 0.3 | 0.3 | 0.3 | 0.3 | 0.3 | 0.3 | 0.3 | 0.3 | 0.3 |
| Cyclomethicone | — | 0.13 | 0.13 | 0.13 | — | — | — | — | — | — | — | — |
| Sodium dodecyl sulfate | — | — | — | — | — | — | — | — | 0.2 | — | — | — |
| Sodium dioctyl sulfosuccinate | 0.2 | 0.2 | — | — | 0.2 | 0.2 | — | — | — | 0.05 | — | 0.2 |
| Sodium lauryl ether sulfate | — | — | — | — | — | — | — | 0.2 | — | — | — | — |
| Cocoamidopropyl betaine | — | — | — | — | — | — | 0.2 | — | — | — | — | — |
| Sodium benzoate | — | 0.0 | 0.144 | 0.3 | 0.3 | — | — | — | — | — | 0.07 | 0.3 |
| Magnesium acetate | — | — | — | — | — | 0.3 | 0.3 | 0.3 | 0.3 | 0.3 | — | — |
| Fragrance | 0.12 | 0.12 | 0.12 | 0.12 | 0.12 | 0.12 | 0.12 | 0.12 | 0.12 | 0.12 | 0.12 | 0.12 |
| Water | to 100 | to 100 | to 100 | to 100 | to 100 | to 100 | to 100 | to 100 | to 100 | to 100 | to 100 | to 100 |

TABLE 2

55% VOC Non-Aerosol Hair Spray Compositions

| | Test Solution # | | | | | | | | | | |
|---|---|---|---|---|---|---|---|---|---|---|---|
| | 13 | 14 | 15 | 16 | 17 | 18 | 19 | 20 | 21 | 22 | 23 |
| Component | | | | | | wt % | | | | | |
| Ethanol | 55.0 | 55.0 | 55.0 | 55.0 | 55.0 | 55.0 | 55.0 | 55.0 | 55.0 | 55.0 | 55.0 |
| 2-amino,2-methyl,1-propanol | 0.84 | 0.84 | 0.74 | 0.74 | 0.74 | 0.74 | 0.74 | 0.74 | 0.74 | 0.74 | 0.37 |
| HC 7801 | 6.0 | 6.0 | 6.0 | 6.0 | 6.0 | 6.0 | 6.0 | 6.0 | 6.0 | 6.0 | 3.0 |
| Dimethicone copolyol | — | — | 0.3 | 0.3 | 0.3 | 0.3 | 0.3 | 0.3 | 0.3 | 0.3 | 0.3 |

TABLE 2-continued

55% VOC Non-Aerosol Hair Spray Compositions

| | Test Solution # | | | | | | | | | | |
|---|---|---|---|---|---|---|---|---|---|---|---|
| Component | 13 | 14 | 15 | 16 | 17 | 18 | 19 | 20 | 21 | 22 | 23 |
| | wt % | | | | | | | | | | |
| Cyclomethicone | — | — | 0.13 | 0.13 | 0.13 | 0.13 | 0.13 | — | — | — | — |
| Sodium dodecyl sulfate | — | — | — | — | — | — | — | 0.2 | — | — | — |
| Sodium dioctyl sulfosuccinate | 0.2 | 0.4 | — | 0.2 | 0.2 | — | — | — | 0.05 | — | 0.2 |
| Sodium lauryl ether sulfate | — | — | — | — | — | — | 0.2 | — | — | — | — |
| Cocoamidopropyl betaine | — | — | — | — | — | 0.2 | — | — | — | — | — |
| Sodium benzoate | 0.144 | 0.144 | — | 0.144 | — | — | — | — | — | 0.07 | 0.3 |
| Magnesium acetate | — | — | — | — | 0.144 | 0.144 | 0.144 | 0.144 | 0.3 | — | — |
| Fragrance | 0.12 | 0.12 | — | 0.12 | 0.12 | 0.12 | 0.12 | 0.12 | 0.12 | 0.12 | 0.12 |
| Water | to 100 | to 100 | to 100 | to 100 | to 100 | to 100 | to 100 | to 100 | to 100 | to 100 | to 100 |

TABLE 3

55% VOC Aerosol Hair Spray Compositions

| | Test Solution # | | | | | | | | | | |
|---|---|---|---|---|---|---|---|---|---|---|---|
| Component | 24 | 25 | 26 | 27 | 28 | 29 | 30 | 31 | 32 | 33 | 34 |
| | wt % | | | | | | | | | | |
| Ethanol | 22.0 | 22.0 | 22.0 | 22.0 | 22.0 | 22.0 | 22.0 | 22.0 | 22.0 | 22.0 | 22.0 |
| 2-amino,2-methyl,1-propanol | 0.56 | 0.56 | 0.56 | 0.56 | 0.56 | 0.56 | 0.56 | 0.56 | 0.56 | 0.56 | 0.29 |
| Resyn 28-2930 | 5.7 | 5.7 | 5.7 | 5.7 | 5.7 | 5.7 | 5.7 | 5.7 | 5.7 | 5.7 | 3.0 |
| Dimethicone copolyol | 0.3 | 0.3 | 0.3 | 0.3 | 0.3 | 0.3 | 0.3 | 0.3 | 0.3 | 0.3 | 0.3 |
| Cyclomethicone | 0.13 | 0.13 | 0.13 | — | — | — | — | — | — | — | — |
| Sodium dodecyl sulfate | — | — | — | — | — | — | — | 0.2 | — | — | — |
| Sodium dioctyl sulfosuccinate | 0.2 | — | — | 0.2 | 0.2 | — | — | — | 0.05 | — | 0.2 |
| Sodium lauryl ether sulfate | — | — | — | — | — | — | 0.2 | — | — | — | — |
| Cocoamidopropyl betaine | — | — | — | — | — | 0.2 | — | — | — | — | — |
| Sodium benzoate | 0.0 | 0.144 | 0.3 | 0.3 | — | — | — | — | — | 0.07 | 0.3 |
| Magnesium acetate | — | — | — | — | 0.3 | 0.3 | 0.3 | 0.3 | 0.3 | — | — |
| Fragrance | 0.12 | 0.12 | 0.12 | 0.12 | 0.12 | 0.12 | 0.12 | 0.12 | 0.12 | 0.12 | 0.12 |
| Dimethyl ether | 33.0 | 33.0 | 33.0 | 33.0 | 33.0 | 33.0 | 33.0 | 33.0 | 33.0 | 33.0 | 33.0 |
| Water | to 100 | to 100 | to 100 | to 100 | to 100 | to 100 | to 100 | to 100 | to 100 | to 100 | to 100 |

TABLE 4

55% VOC Aerosol Hair Spray Compositions

| | Test Solution # | | | | | | | | | | |
|---|---|---|---|---|---|---|---|---|---|---|---|
| Component | 35 | 36 | 37 | 38 | 39 | 40 | 41 | 42 | 43 | 44 | 45 |
| | wt % | | | | | | | | | | |
| Ethanol | 22.0 | 22.0 | 22.0 | 22.0 | 22.0 | 22.0 | 22.0 | 22.0 | 22.0 | 22.0 | 22.0 |
| 2-amino,2-methyl,1-propanol | 0.74 | 0.74 | 0.74 | 0.74 | 0.74 | 0.74 | 0.74 | 0.74 | 0.74 | 0.74 | 0.37 |
| Amphomer LV-71 | 2.5 | 2.5 | 2.5 | 2.5 | 2.5 | 2.5 | 2.5 | 2.5 | 2.5 | 2.5 | 1.25 |
| Resyn 28-2930 | 2.5 | 2.5 | 2.5 | 2.5 | 2.5 | 2.5 | 2.5 | 2.5 | 2.5 | 2.5 | 1.25 |
| Dimethicone copolyol | — | — | 0.3 | 0.3 | 0.3 | 0.3 | 0.3 | 0.3 | 0.3 | 0.3 | 0.3 |
| Cyclomethicone | — | — | 0.13 | 0.13 | 0.13 | 0.13 | 0.13 | — | — | — | — |
| Sodium dodecyl sulfate | — | — | — | — | — | — | — | 0.2 | — | — | — |
| Sodium dioctyl sulfosuccinate | 0.2 | 0.4 | — | 0.2 | 0.2 | — | — | — | 0.05 | — | 0.2 |
| Sodium lauryl ether sulfate | — | — | — | — | — | — | 0.2 | — | — | — | — |
| Cocoamidopropyl betaine | — | — | — | — | — | 0.2 | — | — | — | — | — |
| Sodium benzoate | 0.144 | 0.144 | — | 0.144 | — | — | — | — | — | 0.07 | 0.3 |
| Magnesium acetate | — | — | — | — | 0.144 | 0.144 | 0.144 | 0.144 | 0.3 | — | — |
| Fragrance | 0.12 | 0.12 | — | 0.12 | 0.12 | 0.12 | 0.12 | 0.12 | 0.12 | 0.12 | 0.12 |
| Dimethyl ether | 33.0 | 33.0 | 33.0 | 33.0 | 33.0 | 33.0 | 33.0 | 33.0 | 33.0 | 33.0 | 33.0 |
| Water | to 100 | to 100 | to 100 | to 100 | to 100 | to 100 | to 100 | to 100 | to 100 | to 100 | to 100 |

EXAMPLE 1

Comparison of Dynamic Surface Tension of 55% VOC
Test Hair Spray Solutions with Commercial Hair Sprays

| Test Solution | Dynamic Surface Tension, mN/m | | |
|---|---|---|---|
| | 10 msec | 1500 msec | $\Delta_{10-1500}$ |
| 1 | 38.2 | 26.4 | 11.8 |
| 2 | 35.3 | 23.6 | 11.7 |
| 3 | 36.4 | 24.8 | 11.6 |
| 4 | 36.2 | 24.6 | 11.6 |
| 5 | 34.2 | 24.0 | 10.2 |

$\Delta_{10-1500}$ for commercial Rave 4 = 10.2 ± 0.15 (average of five readings)
$\Delta_{10-1500}$ for commercial Suave Max. hold = 7.3

This example shows that a combination of an organic salt (sodium benzoate) and a hydrocarbon surfactant is required (Test solution #5) to bring the surface tension difference of the 55% VOC test solution down to that of 80% VOC commercial product. Test solution 1 in which only a hydrocarbon based surfactant is used, Test solution #2 in which combination of silicone and hydrocarbon surfactants is present or test solutions 3 and 4, in which a combination of an organic salt and a silicone based surfactant is present do not bring the surface tension difference to that of the 80% VOC product.

EXAMPLE 2

Comparison of Sodium Benzoate and Magnesium Acetate

| Test Solution | Dynamic Surface Tension, mN/m | | |
|---|---|---|---|
| | 10 msec | 1500 msec | $\Delta_{10-1500}$ |
| 5 | 34.2 | 24.0 | 10.2 |
| 6 | 34.7 | 24.0 | 10.5 |

These results show that both sodium benzoate and magnesium acetate brings the surface tension difference of the 55% VOC test solution closer to that of the commercial product.

EXAMPLE 3

Effect of Different Surfactants on Dynamic Surface Tension

| Test Solution | Dynamic Surface Tension, mN/m | | |
|---|---|---|---|
| | 10 msec | 1500 msec | $\Delta_{10-1500}$ |
| 6 | 34.7 | 24.0 | 10.5 |
| 7 | 34.1 | 23.4 | 10.7 |
| 8 | 35.1 | 24.6 | 10.5 |
| 9 | 34.6 | 24.3 | 10.3 |

This example shows that all the hydrocarbon surfactants tested bring down the surface tension difference closer to that of a commercial product.

EXAMPLE 4

Comparison of Effect of Silicone Versus Hydrocarbon Based
Surfactant and Organic Salt on Dynamic Surface Tension

| Test Solution | Dynamic Surface Tension, mN/m | | |
|---|---|---|---|
| | 10 msec | 1500 msec | $\Delta_{10-1500}$ |
| 13 | 35.6 | 25.7 | 9.9 |
| 14 | 34.6 | 25.2 | 9.4 |
| 15 | 35.6 | 24.2 | 11.4 |
| 16 | 33.1 | 23.2 | 9.9 |

This example shows that a combination of hydrocarbon surfactant and an organic salt brings down the surface tension difference down to that of commercial product, also with HC 7801 styling resin. In the absence of hydrocarbon surfactant and an organic salt the surface tension difference remains high (>11).

EXAMPLE 5

Comparison of Sodium Benzoate and Magnesium Acetate

| Test Solution | Dynamic Surface Tension, mN/m | | |
|---|---|---|---|
| | 10 msec | 1500 msec | $\Delta_{10-1500}$ |
| 16 | 33.1 | 23.2 | 9.9 |
| 17 | 33.0 | 22.5 | 10.5 |

These results show that both sodium benzoate and magnesium acetate bring the surface tension difference of the 55% VOC test solution closer to that of the commercial product, also with HC 7801 styling resin.

EXAMPLE 6

Effect of Different Surfactants on Dynamic Surface Tension

| Test Solution | Dynamic Surface Tension, mN/m | | |
|---|---|---|---|
| | 10 msec | 1500 msec | $\Delta_{10-1500}$ |
| 17 | 33.0 | 22.5 | 10.5 |
| 18 | 33.7 | 23.6 | 10.1 |
| 19 | 33.9 | 23.1 | 10.8 |
| 20 | 33.7 | 23.1 | 10.6 |

This example shows that all the hydrocarbon surfactants tested bring down the surface tension difference closer to that of commercial product, also with HC 7801 styling resin.

EXAMPLE 7

Effect of Different Levels of Polymers and
Surfactants on Dynamic Surface Tension

| Test Solution | Dynamic Surface Tension, mN/m | | |
|---|---|---|---|
| | 10 msec | 1500 msec | $\Delta_{10-1500}$ |
| 10 | 36.1 | 25.8 | 10.3 |
| 12 | 32.1 | 22.6 | 9.5 |
| 21 | 34.2 | 24.2 | 10.0 |
| 23 | 33.0 | 23.1 | 9.9 |

This example shows that the combination of organic salt and the hydrocarbon based surfactant shows synergy at low polymer level of 3.0% and also low dioctyl sulfosuccinate level of 0.05 wt %.

EXAMPLE 7(a)

Comparison of Composition of Test Solution #15 with Commercial Product Rave
4 in Consumer Test of Spray Characteristics Test Type: Mini take home test
Number of consumers: 38
Rating Scale: 0 to 9; 0 — very poor & 9 — very good

| Sequential monadic question | Rating Significance | | |
|---|---|---|---|
| | Commercial Product | Test Product | |
| How easy is it to control the direction of the spray? | 7.2 | 6.2 | 90% |
| How easy is it to control the amount of spray? | 6.3 | 5.4 | 99% |
| How fine is the mist? | 6.2 | 5.5 | 90% |
| How even is the spray? | 6.6 | 5.7 | 95% |
| How easy is it to get the first spray? | 6.0 | 5.0 | 95% |
| How fast does the product dry? | 6.8 | 5.4 | 99% |
| How manageable does the product make your hair? | 5.6 | 4.3 | 95% |
| Surface tension difference, $\Delta_{10-1500}$ | 10.2 | 11.4 | |

The consumer test results show that the test solution with higher surface tension difference performs poorly compared to the commercial product with a lower surface tension difference.

EXAMPLE 8

Comparison of Composition of Test Solution #16 with Commercial Product in
Consumer Test of Spray Characteristics Test Type: Mini take home test
Number of consumers: 39
Rating Scale: 0 to 9; 0 — very poor & 9 — very good

| Sequential monadic question | Rating Significance | | |
|---|---|---|---|
| | Commercial product | Test Product | |
| How easy is it to control the direction of the spray? | 6.1 | 6.5 | No diff. |
| How easy is it to control the direction of the spray? | 5.7 | 5.8 | No diff. |
| How fine is the mist? | 6.0 | 5.7 | No diff. |
| How even is the spray? | 6.0 | 6.1 | No diff. |
| How easy is it to get the first spray? | 4.2 | 4.4 | No diff. |
| How fast does the product dry? | 5.6 | 5.2 | No diff. |
| How manageable does the product make your hair? | 5.1 | 4.7 | No diff. |
| Surface tension difference, $\Delta_{10-1500}$ | 7.3 | 9.9 | |

These results show that as the surface tension difference of the 55% VOC test solution is reduced to about 10.0, it performs as well as the 80% VOC commercial product.

What is claimed is:

1. An aqueous non-aerosol hair styling composition having 55% or less VOC content, said composition comprising (i) a water soluble or dispersable fixative polymer of about 10 to about 1000 Kilo Daltons and in an amount ranging from 1% to 40% by weight of the composition; (ii) a neutralizing agent in an amount ranging from 0.1 to 10% by weight and selected from the group consisting of 2-amino, 2-methyl, 1-propanol; dimethyl stearamine; sodium hydroxide; and potassium hydroxide; (iii) a surfactant in an amount ranging from 0.01% to 5% by weight and selected from the group consisting of sodium dioctyl sulfo succinate, sodium dodecyl sulfate, cocoamidopropyl betaine, and sodium laureth sulfate; (iv) a salt ranging from 0.01% to 10% by weight and selected from the group consisting of sodium benzoate, and magnesium acetate; (v) an alcohol ranging from 10% to 90% by weight; and (vi) water ranging from 10% to 90% by weight.

2. A composition according to claim 1 wherein the polymer is in the molecular weight range of about 20 to 500 Kilo Daltons.

3. A composition according to claim 1 wherein the polymer is in the molecular weight range of about 50 to about 300 Kilo Daltons.

4. A composition according to claim 1 in which the polymer is a polymer selected from the group consisting of ethyl acrylate, methyl methacrylate and methacrylic acid copolymer; ethyl acrylate, t-butyl acrylate and methacrylic acid terpolymer; octyl acrylamide, acrylates and butylaminoethyl methacrylate copolymer; methacrylic acid, n-butyl acrylate and methyl methacrylate copolymer; methacrylic acid, n-butyl acrylate and ethyl methacrylate copolymer; butyl acrylate, methyl methacrylate, hydroxyethyl methacrylate and methacrylic acid copolymer; vinyl acetate, crotonates and vinyl neodecanoate copolymer; a butyl ester of vinyl methyl ether and maleic anhydride copolymer; an ethyl ester of vinyl methyl ether and maleic anhydride copolymer; a polymer which consists of polystyrene sulfonate monomers; a polymer consists of 1-vinyl-2- pyrrolidone; vinyl acetate and vinylpyrrolidone copolymer; vinylcaprolactam homopolymer; a quaternary ammonium polymer formed by the reaction of diethyl sulfate and a copolymer of vinyl pyrrolidone and dimethyl aminoethyl-methacrylate; and mixtures thereof.

5. The composition according to claim 1 wherein the alcohol is selected from the group consisting of ethanol and isopropanol.

6. A composition according to claim 1 which further comprises silicone based surfactants in an amount from 0.01% to 5% by weight of the composition.

7. The compositions in claim 1 in which the silicone based surfactant is selected from the group consisting of dimethicone copolyol and cyclomethicone.

* * * * *